United States Patent [19]

Sieburth

[11] Patent Number: 4,709,068
[45] Date of Patent: Nov. 24, 1987

[54] SUBSTITUTED PHENYLTRIALKYLSILANE INSECTICIDES

[75] Inventor: Scott M. Sieburth, Princeton, N.J.

[73] Assignee: FMC Corporation, Philadelphia, Pa.

[21] Appl. No.: 869,797

[22] Filed: Jun. 2, 1986

[51] Int. Cl.$^4$ ............................ C07F 7/08; C07F 7/18
[52] U.S. Cl. .................................... 556/447; 514/63; 549/4; 549/215; 549/214
[58] Field of Search .............. 556/447; 514/63; 549/4, 549/214, 215

[56] References Cited

U.S. PATENT DOCUMENTS 3,770,790  11/1973  Clark .................................... 556/447
4,481,365  11/1984  Förster et al. .................. 556/447 X

FOREIGN PATENT DOCUMENTS 0123491  7/1985  Japan ............................ 556/447 UX
087687A  5/1986  Japan ............................ 556/447 UX
2120664  5/1983  United Kingdom ........ 556/447 UX
0276957  7/1970  U.S.S.R. .............................. 556/447

Primary Examiner—Paul F. Shaver
Attorney, Agent, or Firm—William Schmonsees; H. Robinson Ertelt

[57] ABSTRACT

Compounds containing a dimethylsilane core and a phenoxybenzyl substituent are found to exhibit pyrethroid-like activity toward insects with low toxicity to fish.

10 Claims, No Drawings

SUBSTITUTED PHENYLTRIALKYLSILANE INSECTICIDES

BACKGROUND OF THE INVENTION

This invention relates to novel pyrethroid-like insecticides, which effectively control infestations of undesirable insects, while displaying remarkably low toxicity to fish. Synthetic pyrethroids have been the focus of intensive research efforts for the past decade. The pioneering work of Elliott, as described in U.S. Pat. No. 4,024,163, established that synthetic pyrethroids could be synthesized with sufficient stability to light to be commercially attractive. Since that time, a large number of variations on the basic pyrethroid structure have been developed. The vast majority of these new pyrethroids retain the cyclopropane ring of the natural pyrethroids, initially considered a necessity for insecticidal activity. Some effort has been directed towards defining other compounds which are nominally described as pyrethroids based upon similar molecular geometry. The current invention discloses a new synthetic pyrethroid having a dimethylsilane core. Prior to this development, there was no indication that a dimethylsilane compound would display pyrethroid-like activity. Further, the fact that the silane compound has almost one one-thousandth the toxicity to fish that cyclopropane carboxylate pyrethroids have solves one of the outstanding problems of pyrethroid insecticide development.

DESCRIPTION OF RELATED ART

U.K. Patent Application No. 2120664A discloses a variety of pyrethroid insecticides which are alleged to have low toxicity towards fish. The compounds of this U.K. disclosure, while having similarities to that of the present invention, are all based upon previously known pyrethroid-like insecticides. The compounds disclosed all have a dimethylcarbon center.

There is no indication in the art that any silicon-containing compound would display pyrethroid-like insecticidal activity. It is even more surprising, then, that silane-containing pyrethroids which have insecticidal activity also display low toxicity towards fish.

SUMMARY OF THE INVENTION

The compounds of this invention may be generally described as substituted phenyltrialkylsilanes, having a 3-phenoxyphenyl group bonded to the silicon atom through at least a three atom chain.

This invention also encompasses insecticidal compositions containing the substituted silanes and their use for controlling insects. The compounds of this invention are effective for control of a wide variety of insects and may be expected to be useful in any situation in which pyrethroid insecticides are indicated. The compounds of this invention find particular utility in applications wherein there is a possibility of substantial runoff of the insecticidal material into streams, rivers, and lakes. The low fish toxicity of these compounds will obviate concern about potential ecological problems associated with the use of pyrethroids in environments where substantial runoff is possible.

DETAILED DESCRIPTION

The substituted phenyltrialkylsilanes have the general formula,

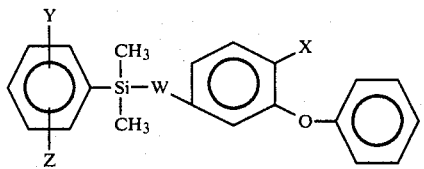

wherein Y is alkyl, alkoxy, halogen, or haloalkoxy, Z is hydrogen, halogen, alkyl, alkoxy, or haloalkoxy, or Y and Z together form the group —A—(CR$_1$R$_2$)$_n$—A— where R$_1$ and R$_2$ are independently hydrogen, halogen, or alkyl, n=1 or 2, and each A may be O, S, or CH$_2$. W is a —CH$_2$CH$_2$CH$_2$— or —CH$_2$OCH$_2$— group and X is fluorine or hydrogen.

Suitable Y groups include methyl, ethyl, methoxy, ethoxy, isopropoxy, 2-fluoroethoxy, fluorine, and chlorine. Ethoxy and 2-fluoroethoxy groups are preferred. Z is preferably hydrogen or chlorine. W is preferably a —CH$_2$CH$_2$CH$_2$— group and X is preferably fluorine.

The syntheses of (4-ethoxyphenyl)[3-(4-fluoro-3-phenoxyphenyl)propyl]dimethylsilane and of (4-fluoro-3-phenoxyphenyl)methyl 2-(4-ethoxyphenyl)-2-methyl-2-silapropyl ether are described in the following examples. Other simple modifications of these compounds may be prepared by obvious variations of the basic process.

EXAMPLE 1

Synthesis of (4-ethoxyphenyl)[3-(4-fluoro-3-phenoxyphenyl)-propyl]dimethylsilane Part A. Preparation of ethyl 3-(4-fluoro-3-phenoxyphenyl)acrylate In a flask were placed 15 g (0.069 mole) of 4-fluoro-3-phenoxybenzaldehyde, 25 g (0.072 mole) of ethyl (triphenylphosphoranylidene)acetate, and 150 ml of tetrahydrofuran. This mixture was stirred at room temperature for four hours. It was then filtered, the filtrate concentrated, and the residue diluted with hexane. Filtration and concentration of this mixture yielded 23.5 g of a yellow oil composed primarily of ethyl 3-(4-fluoro-3-phenoxyphenyl)acrylate. This oil changed color upon standing, becoming a fluorescent pink.

Part B. Preparation of 3-(4-fluoro-3-phenoxyphenyl)-propanol

To a suspension of 5 g (0.13 mole) of lithium aluminum hydride in 200 ml of dry diethyl ether was added dropwise 22 g of crude ethyl 3-(4-fluoro-3-phenoxyphenyl)acrylate (Part A) in 50 ml of diethyl ether. This mixture was stirred overnight. Sequentially, 5 ml of water, 5 ml of 15% sodium hydroxide in water, and 15 ml of water were added to the reaction mixture. The mixture was filtered to remove the solid which precipitated. This solid was extracted once with hot tetrahydrofuran and the extract was combined with the filtrate. Concentration of this mixture yielded 18.8 g of a semi-solid material which was passed through a column of silica gel, eluting with hexane/ethyl acetate (1:1). Combination of the appropriate fractions and evaporation of the solvent yielded 14.4 g of 3-(4-fluoro-3-phenoxyphenyl)-1-propanol as a colorless oil.

Part C. Preparation of 1-bromo-3-(4-fluoro-3-phenoxyphenyl)propane

To 5.30 g (0.0215 mole) of 3-(4-fluoro-3-phenoxyphenyl)-1-propanol in 18 ml of dry acetonitrile was added first 3.5 g (0.022 mole) of 1,1'-carbonyldiimidazole and then 13.0 g (0.107 mole) of allyl bromide. After stirring at room temperature for 1.5 hours the reaction mixture was heated at gentle reflux for two hours. The reaction mixture was poured into water, and this mixture was extracted twice with diethyl ether. The combined extracts were washed successively with 10% hydrochloric acid, a saturated aqueous solution of sodium bicarbonate, an aqueous solution of sodium thiosulfate, water, and a saturated aqueous solution of sodium chloride. The organic solution was dried over anhydrous magnesium sulfate, filtered, and the solvent was evaporated under reduced pressure, leaving an oil as a residue. The residue was dissolved in approximately 50 ml of hexane and the solution was filtered through a pad of silica gel. Evaporation of the solvent from the filtrate yielded 4.4 g of 1-bromo-3-(4-fluoro-3-phenoxyphenyl)propane as a colorless oil.

Part D. Preparation of chloro(4-ethoxyphenyl)dimethylsilane

To a stirred suspension of 3.5 g (0.14 mole) of magnesium powder in 100 ml of dry tetrahydrofuran was added dropwise 17.5 g (0.14 mole) of p-bromophenyl ethyl ether during a one hour period. The mixture was warmed for one hour and then cooled to room temperature. The reaction mixture was added dropwise to a solution of dichlorodimethylsilane in 100 ml of dry tetrahydrofuran which was cooled to −78° C. Upon completion of addition the reaction mixture was allowed to warm to room temperature. Stirring was continued overnight. After dilution with hexane, the reaction mixture was filtered through celite, and the solvent was evaporated under reduced pressure, leaving a liquid residue. Distillation of this residue yielded 18 g of chloro(4-ethoxyphenyl)dimethylsilane as a clear, colorless oil, b.p. 79°–81° C./0.09 mm of Hg.

Part E. Synthesis of (4-ethoxyphenyl)[3-(4-fluoro-3-phenoyphenyl)propyl]dimethylsilane A small crystal of iodine was added to a mixture of 0.75 g (0.0024 mole) of 1-bromo-3-(4-fluoro-3-phenoxyphenyl)propane and 0.11 g (0.0045 mole) of magnesium powder in 1 ml of tetrahydrofuran. This mixture was heated in a water bath for about three hours. After heating, the clear solution was light grey-brown in color. The solution was cooled to 10° C., and 0.51 g (0.0022 mole) of chloro(4-ethoxyphenyl)dimethylsilane was added. This mixture was stirred for one-half hour and was then heated for an hour. Following dilution with diethyl ether, the reaction mixture was washed successively with 10% hydrochloric acid and a saturated aqueous solution of sodium chloride, dried over anhydrous magnesium sulfate, and filtered. The filtrate was concentrated under reduced pressure, leaving a colorless oil weighing 0.95 g as the residue. This oil was purified using a Chromatotron (eluant=ethyl acetate/hexane (2:98)), producing (4-ethoxyphenyl)[3-(4-fluoro-3-phenoxyphenyl)propyl]dimethylsilane as a colorless oil. The proton and $^{13}C$ nmr spectra were consistent with the proposed structure.

EXAMPLE 2

Synthesis of (4-fluoro-3-phenoxyphenyl)methyl 2-(4-ethoxyphenyl)-2-methyl-2-silapropyl ether Part A. Preparation of (chloromethyl)(4-ethoxyphenyl) dimethylsilane To a mixture of 5.1 g (0.21 mole) of powdered magnesium metal in 100 ml of dry tetrahydrofuran was added dropwise 40 g (0.20 mole) of ethyl 4-bromophenyl ether. Upon completion of addition this mixture was heated at reflux for one hour. In a second flask was placed 28.5 g (0.199 mole) of (chloromethyl)dimethylchlorosilane in 100 ml of tetrahydrofuran, and this flask was cooled to −78° C. The contents of the first flask were added dropwise to the second flask. The temperature of the reaction mixture was maintained at −78° C. for one hour after addition was complete, and it was then poured into 200 ml of 10% hydrochloric acid. The organic phase was washed once with 10% hydrochloric acid. The aqueous phase was extracted with diethyl ether, and these extracts were combined with the organic phase. After being dried, filtered, and having the solvent evaporated under reduced pressure, the residue was vacuum distilled, yielding 10.5 g of (chloromethyl)(4-ethoxyphenyl)dimethylsilane, b.p. 99°–110° C./0.12 mm of Hg. The nmr spectrum was consistent with the proposed structure.

Part B. Preparation of 2-(4-ethoxyphenyl)-2-methyl-2-silapropyl acetate

In a flask under nitrogen were placed 10.1 g (0.044 mole) of (chloromethyl)(4-ethoxyphenyl)dimethylsilane, 4.0 g (0.049 mole) of sodium acetate, 1.2 g (0.0043 mole) of tetrabutylammonium chloride, and 75 ml of carbon tetrachloride. This mixture was refluxed for four days. After cooling to room temperature, 2.0 g (0.024 mole) of sodium acetate and 0.60 g (0.0022 mole) of tetrabutylammonium chloride was added, and the reaction mixture was refluxed for five more days. This mixture was then diluted with diethyl ether, filtered through silica gel, and the solvent was evaporated under reduced pressure, leaving 11.7 g of 2-(4-ethoxyphenyl)-2-methyl-2-silapropyl acetate as a clear, light brown oil. The nmr spectrum was consistent with the proposed structure.

Part C. Preparation of 2-(4-ethoxyphenyl)-2-methyl-2-silapropanol

To 48 ml of a 1M diethyl ether solution of lithium aluminum hydride (1.82 g, 0.048 mole) that had been cooled to 0° C. was added dropwise a solution of 11.0 g (0.044 mole) of 2-(4-ethoxyphenyl)-2-methyl-2-silapropyl acetate in 50 ml of diethyl ether. Fifteen minutes after the addition was complete, the reaction mixture was allowed to warm to room temperature, and it was stirred for 4.5 hours. To the reaction mixture were then added sequentially 1.8 ml of water, 1.8 ml of an aqueous 15% solution of sodium hydroxide, and 5.4 ml of water. Sufficient aqueous 10% sulfuric acid was added to dissolve the undissolved salts, and this mixture was extracted twice with diethyl ether. The combined extracts were washed with water and then with a saturated aqueous sodium carbonate solution that had been diluted with water (50:50). After being dried over anhydrous potassium carbonate and filtered, the solvent was evaporated under reduced pressure, leaving 8.0 g of 2-(4-ethoxyphenyl)-2-methyl-2-silapropanol as an orange oil. The nmr spectrum was consistent with the proposed structure.

Part D. Preparation of (4-fluoro-3-phenoxyphenyl)methyl alcohol

Under argon 2.16 g (0.010 mole) of 4-fluoro-3-phenoxybenzaldehyde was dissolved in 50 ml of absolute ethanol. To this solution was added with stirring 0.28 g (0.0074 mole) of sodium borohydride. After stirring at room temperature for 24 hours, 3 ml of 10% hydrochloric acid was added to the reaction mixture. The solvent was then evaporated under reduced pressure, leaving a milky-white residue. This residue was dissolved in 100 ml of diethyl ether and 5% hydrochloric acid. The organic phase was separated, washed in succession twice with 25 ml of 5% hydrochloric acid and twice with 10 ml of a saturated aqueous solution of sodium chloride, and dried over anhydrous magnesium sulfate. After filtration, the solvent was evaporated under reduced pressure, leaving 1.98 g of (4-fluoro-3-phenoxyphenyl)methyl alcohol as a clear, colorless liquid. The nmr and ir spectra were consistent with the proposed structure.

Part E. Preparation of (4-fluoro-3-phenoxyphenyl)-methyl chloride

In a dry flask were placed in succession 5 ml of diethyl ether, 1.21 g (0.0102 mole) of thionyl chloride, and one drop of pyridine. A solution of 1.85 g (0.0085 mole) of (4-fluoro-3-phenoxyphenyl)methyl alcohol in 5 ml of diethyl ether was added dropwise to the reaction mixture. Upon completion of addition, the reaction mixture was heated at reflux for one hour. After being cooled to room temperature, 10 ml of water was added slowly to the reaction mixture. The phases were separated. Twice the aqueous phase was extracted with 15 ml of diethyl ether, and these extracts were combined with the organic phase. The latter was washed successively twice with 10 ml of a saturated aqueous solution of sodium chloride, once with 10 ml of an aqueous solution of sodium bicarbonate, and twice with the saturated aqueous solution of sodium chloride. After being dried over anhydrous sodium sulfate and being filtered, the solvent was evaporated under reduced pressure, leaving 1.85 g of (4-fluoro-3-phenoxyphenyl)methyl chloride as a light yellow liquid. The nmr and ir spectra were consistent with the proposed structure.

Part F. Synthesis of (4-fluoro-3-phenoxyphenyl)-methyl 2-(4-ethoxyphenyl)-2-methyl-2-silapropyl ether To a solution of 1.0 g (0.0042 mole) of (4-fluoro-3-phenoxyphenyl)methyl chloride in 5 ml of dry toluene was added 0.15 g (0.0063 mole) of sodium hydride. Dropwise a solution of 0.98 g (0.0047 mole) of 2-(4-ethoxyphenyl)-2-methyl-2-silapropanol in 5 ml of dry toluene was added to the reaction mixture. The reaction mixture was stirred at room temperature for one hour and then was heated at reflux for three hours. Aqueous 10% hydrochloric acid was added to the reaction mixture which was then extracted twice with diethyl ether. The combined extracts were dried, filtered through silica gel, and the solvent was evaporated under reduced pressure, leaving a residue. This residue was subjected to Kugelrohr distillation to remove remaining starting materials. The residue from this distillation was separated into two major fractions using a Chromatotron (eluant=ethyl acetate/hexane (2:98). The smaller fraction, weighing 0.19 g, was determined to be (4-fluoro-3-phenoxyphenyl)methyl 2-(4-ethoxyphenyl)-2-methyl-2-silapropyl ether from its nmr spectrum.

In the normal use of the insecticidal silanes of the present invention, the silanes usually will not be employed free from admixture or dilution, but ordinarily will be used in a suitable formulated composition compatible with the method of application and comprising an insecticidally effective amount of silane. The silanes of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present silanes may be applied, for example, as sprays, dusts, or granules to the area where pest control is desired, the type of application varying of course with the pest and the environment. Thus, the silanes of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the silanes. The granule particles are relatively large, a diameter of about 400–2500 microns typically. The particles are either impregnated with the silanes from solution or coated with the silanes, adhesive sometimes being employed. Granules generally contain 0.05–10%, preferably 0.5–5%, active ingredient as the insecticidally effective amount.

Dusts are admixtures of the silanes with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of silane and 99 parts of talc.

The silanes of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% silane, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of (4-ethoxyphenyl)[3-(4-fluoro-3-phenoxyphenyl)propyl]dimethylsilane, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the silane with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfates of higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal composition.

Other useful formulations include simple solutions of the active ingredient in a solvent in which it is completely soluble at the desired concentrations, such as acetone or other organic solvents.

An insecticidally effective amount of silane in an insecticidal composition diluted for application is normally in the range of about 0.001% to about 8% by weight. Many variations of spraying and dusting compositions known in the art may be used by substituting the silanes of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of silane be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

The insecticidal activity of the silanes of Examples 1 and 2 was evaluated as follows:

The compound was tested by foliar application at various concentrations in aqueous solutions containing 10% acetone and 0.25% octyl phenoxypolyethoxy ethanol. The evaluation utilized Mexican bean beetle (*Epilachna varivestis*), southern armyworm (*Spodoptera eridania*), and pea aphid (*Acyrthosiphon pisum*).

In the cases of Mexican bean beetle and southern armyworm, pinto bean plants were placed on a revolving turntable in a hood, and the test solutions were applied with a sprayer. The test solutions were applied to the upper and lower surfaces of the plant leaves to runoff. The plants were then allowed to dry and were severed at the base of the stem before being placed in cups. Ten individuals of the appropriate insect species were placed in each cup and the cup covered. Mortality was read 48 hours later.

Fava bean was substituted for pinto bean in the case of pea aphid, and the treated, potted plants were placed in cups infested with ten individuals, and covered. Mortality was read 48 hours later.

The results of the tests are shown below:

| Compound of Example | Active Ingredient Concentration | % Kill | | |
|---|---|---|---|---|
| | | Mexican Bean Beetle | Pea Aphid | Southern Armyworm |
| 1 | 64 ppm | 100 | 30 | 100 |
| 2 | 64 ppm | 100 | — | 100 |

SOIL EVALUATION

A stock solution of the test compound is prepared by dissolving 4.8 mg in 10 ml of acetone and diluting with 90 ml of acetone/water (1:9). The addition of 5 ml of this stock solution to 30 g of air-dried, clay loam soil in a 3 oz plastic cup provides a concentration of 8 ppm of the test compound in the soil. Serial dilution of the stock solution is used to provide concentrations of the test compound in soil of 4, 2, 1, 0.5, and 0.25 ppm. In all cases 5 ml of a solution having the required concentration is added to 30 g of soil. The treated soil is allowed to stand uncovered in a hood for 0.5 hour to evaporate the acetone. Before infesting the soil with southern corn rootworm larvae (*Diabrotica undecimpunctata howardi Barber*) the soil is mixed thoroughly and two three-day-old corn sprouts are planted in it. Ten early third-stage (9-10 days old) southern corn rootworm larvae are placed in the cup which is covered with a plastic lid, and the cup is placed in a closed plastic bag. After storage at 74°-78° F. for 48 hours, the mortality of the larvae is determined by removing the cup from the plastic bag, removing the cover, and placing the cup in a modified Berlese polyethylene funnel fitted with an 18-mesh screen. The funnels are placed over containers of an aqueous detergent solution. Incandescent lights (100 watts) are placed 36 cm above the soil samples. The heat from these lights slowly dries the soil which causes larvae that have not been affected by the test compound to emerge from the soil and drop into the detergent solution. The percent mortality is determined in this manner for each concentration.

The residual activity of the test compounds is determined in the same manner as the initial evaluation except that treated soil is not infested with larvae until 7 days after treatment.

The test was run in duplicate, and indicated an initial $LC_{50}$ of 1.50 ppm for the compound of Example 1. After seven days, the test compound continued to show activity, killing 85% of the larvae at a concentration of 4 ppm.

FISH TOXICITY

The toxicity towards fish was determined in a standard 48 hour static bioassay using the bluegill sun fish (*Lepomis macrochirus*). Ten fish ranging in size from 1 to 2 inches were used and each test chamber contained the specified concentration of compound. Each 40 liter aquarium contained 20 liters of test solution, with a loading of one fish per 2 liters, in accordance with the EPA organism loading limit. The fish used were held in soft reconstituted water at 24° C. for at least two weeks prior to testing.

After 48 hours in the tank, the percent kill was determined and an $LD_{50}$ calculated therefrom.

In addition to the compound of Example 1, compound 3 of British application GB2120664A was tested for fish toxicity. The reference standard for comparison to conventional pyrethroid insecticides was cypermethrin, a compound widely used in crop protection.

The compound of Example 1 exhibited 0% kill at a loading of 50 ppm. This may be interpreted as showing an $LD_{50}$ of greater than 50 ppm. In contrast, compound 3 of the British application showed 100% kill at 50 ppm and 80% kill at 10 ppm. This test yields an $LD_{50}$ of 3.1 ppm for the carbon-containing compound. Comparatively, the silicon-containing compound is less than one-sixteenth as toxic to fish as the carbon-containing pyrethroid. Cypermethrin displayed 100% kill at a concentration of 0.01 ppm.

The remarkably low toxicity towards fish of the dimethylsilanes is certainly unexpected and this factor, in combination with the demonstrated insecticidal activity, should make them appropriate compounds for control of insect infestations in aquatic environments, such as rice paddies.

I claim:

1. A compound of the formula

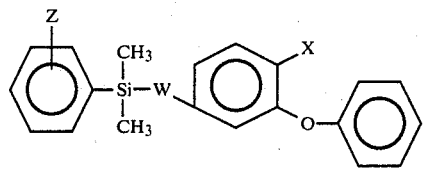

wherein Y is alkyl, alkoxy, halogen, or haloalkoxy, Z is hydrogen, halogen, alkyl, alkoxy, or haloalkoxy, or Y and Z together form the group —A—$(CR_1R_2)_n$—A— where $R_1$ and $R_2$ are independently hydrogen, halogen, or alkyl, n=1 or 2, and each A may be O, S, or $CH_2$; W is a —$CH_2CH_2CH_2$— group; and X is fluorine or hydrogen.

2. A compound of claim 1 in which Y is alkoxy.

3. A compound of claim 2 in which Y is ethoxy and X is fluorine.

4. A compound of claim 3 in which Z is hydrogen or chlorine.

5. A compound of claim 1 in which Y is haloalkoxy.

6. A compound of claim 5 in which Y is 2-fluoroethoxy and X is fluorine.

7. A compound of claim 6 in which Z is hydrogen or chlorine.

8. The compound (4-ethoxyphenyl)[3-(4-fluoro-3-phenoxyphenyl)propyl]dimethylsilane.

9. An insecticidal composition comprising an insecticidally effective amount of a compound of claim 1 in admixture with a compatible agricultural carrier, diluent, or adjuvant.

10. A method for controlling insects by application to the locus where control is desired an insecticidally effective amount of a compound of claim 1.

* * * * *

UNITED STATES PATENT AND TRADEMARK OFFICE
CERTIFICATE OF CORRECTION

PATENT NO. : 4,709,068
DATED : November 24, 1987
INVENTOR(S) : Scott M. Sieburth It is certified that error appears in the above-identified patent and that said Letters Patent is hereby corrected as shown below:

In the claims, Claim 1, column 10, structure should read as follows:

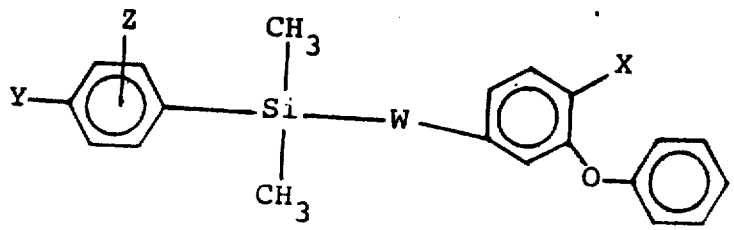

Signed and Sealed this

Seventeenth Day of May, 1988

Attest:

DONALD J. QUIGG

Attesting Officer

Commissioner of Patents and Trademarks